US006726913B1

(12) United States Patent
Van Kampen et al.

(10) Patent No.: US 6,726,913 B1

(45) Date of Patent: Apr. 27, 2004

(54) **TREATMENT OF DERMAL TUMORS, WARTS, AND VIRAL INFECTIONS OF THE RESPIRATORY TRACT IN HUMANS USING HEAT-KILLED *P. ACNES***

(75) Inventors: Kent R. Van Kampen, Hoover, AL (US); Bobby G. Edwards, Salado, TX (US)

(73) Assignee: The Van Kampen Group, Inc., Hoover, AL (US)

( * ) Notice: Subject to any disclaimer, the term of this patent is extended or adjusted under 35 U.S.C. 154(b) by 0 days.

(21) Appl. No.: 09/689,621

(22) Filed: Oct. 13, 2000

(Under 37 CFR 1.47)

Related U.S. Application Data

(60) Provisional application No. 60/159,567, filed on Oct. 15, 1999.

(51) Int. Cl.[7] ................................................ A61K 45/00

(52) U.S. Cl. ................ 424/282.1; 424/93.4; 424/184.1; 435/252.1

(58) Field of Search ............................ 424/184.1, 93.4; 435/282.1, 252.1

(56) References Cited

U.S. PATENT DOCUMENTS

| | | | |
|---|---|---|---|
| 4,360,510 A | * | 11/1982 | Proctor |
| 4,479,935 A | | 10/1984 | Metianu et al. |
| 4,746,511 A | | 5/1988 | Kobatake et al. |
| 4,873,090 A | | 10/1989 | Clancy |
| 6,019,985 A | | 2/2000 | Brown et al. |
| 6,221,847 B1 | | 4/2001 | Barefoot et al. |

OTHER PUBLICATIONS

U.S. patent application Ser. No. 08/912,026, Oral Administration of Bacteria at a Concentration Which Produces Cell—Mediated Immunity and Weight Gain in Certain Animals.

Adlam C. and M.T. Scott, Lympho–reticular stimulatory properties of corynebacterium parvum and related bacteria, J. Med. Microbiol., 6(3):261–74 (1973).

Becker A. et al., Propionibacterium acnes immunotherapy in chronic recurrent canine pyoderma, J. Vet. Intern. Med., 3(1):26–30 (1989).

Bellanti J. and J. Clot, Advances in Ribosomal Immunotherapy, Drugs Supplement, Adis International 51:Supp 1, 1–49 (1997).

Christie, G.H. and R. Bomford, Mechanisms of macrophage activation by Corynebacterium parvum, Cell. Immuno., 17:141–49 (1975).

Cox WI, Examining the immunologic and hematopoietic properties of an immunostimulant, Veterinary Medicine, p. 424–428 (1988).

Evans, D.R. et al., Inactivated Propionibacterium acnes (ImmunoRegulin) as adjunct to conventional therapy in the treatment of equine respiratory diseases, Equine Practice, 10 (6):17–21 (1988).

Flamino MJ et al., Immunologic function in horses after non–specific immunostimulation administration, Vet. Immonl. Immunopathol., 63(4):303–15 (1998).

Fujiwara H. et al., Preventative effect of Propionibacterium acnes on metastasis in mice rendered tolerant to tumor–associated transplantation antigens, Gann., 71(5):692–8 (1980).

Hall H. et al., Induced regression of bovine papillomas by intralesional immunotherapy, Ther. Immunol., 1(6):319 (1994).

Hollingshead AC and Stewart TH, Specific and nonspecific immunotherapy as an adjunct to curative surgery for cancer of th lung, Yale J. Biol. Med., 54(5):367–79 (1981).

Howard, J.G. et al., Biological Effects of Corynebacterium, parvum, Cell. Immuno. 7, 290–301 (1973).

Jackson RA et al., Role of pulmonary macrophages in resistance to experimental metastasis, J. Leukoc. Biol., 40(5):575–87 (1986).

Lynch NR and Salomon JC, Tumor growth inhibition and potentiation of immunotherapy by indomethacin in mice, J. Natl. Cancer Inst., 62(1):117–21 (1979).

Masuhara M. J., Expression of hepatocyte growth factor and transforming growth factor beta 1 mRNA in P. acnes and lipopolysaccharide–treated rats, J. Gastroenterol., 30(1):48–54 (1995).

(List continued on next page.)

*Primary Examiner*—Leon B. Lankford, Jr.

(74) *Attorney, Agent, or Firm*—Brian J. Laurenzo; Michael C. Gilchrist; Jason M. Hunt

(57) ABSTRACT

Heat-killed, terminally sterilized saline suspensions of *Propionibacterium acnes, Propionibacterium avidum, Propionibacterium lymphophilum, Propionibacterium granulosum, Cornynebacterium parvum,* and *Arachnia propionica* are effective in treating viral infections of the respiratory tract in humans, and to induce the regression of dermal tumors and warts in humans. The potency of a saline suspension of heat-killed, terminally sterilized saline suspension of *Propionibacterium acnes* (*P. acnes*) was demonstrated through a laboratory animal challenge model. The *P. acnes* product is administered orally for the purpose of preventing or treating viral infections of the respiratory tract in man. The *P. acnes* preparation is intralesionally administered into dermal tumors, warts such as plantar warts, or other warts in people caused by the human papilloma virus, to cause regression of such dermal tumors and warts. The subcutaneous route of administration of the *P. acnes* product causes a systemic reaction that causes long-term warts to completely regress. Anesthetics such as Lidocaine may be added to the *P. acnes* product to prevent pain upon injection of this immune modulating preparation, while retaining the potency of the *P. acnes* product. Dose ranges have been established for the oral administration of the *P. acnes* product to treat viral infections, and for the subcutaneous and intralesional administration of the *P. acnes* product to treat dermal tumors and warts.

19 Claims, No Drawings

OTHER PUBLICATIONS

Megid J and Kaneno R, Natural killer activity in mice infected with rabies virus and submitted to P. acnes (Propionibacterium acnes) as immunomodulator, Comp. Immunol. Microbiol. Infect. Dis., 23(2):91–7 (2000).

Megid J et al., Effect of bacillus of Calmette–Guerin, avridine and Propionibacterium acnes as immunomodulators on rabies in mice, Rev Inst. Med. Trop. Sao Paulo, 41(2):107–14 (1999).

Megid J et al., Effect of the bacillus of Calmette–Guerin, Propionibacter acnes and avridine as immunomodulators in antirabies vaccination of mice using the Fuenzalide–Palacios mouse brain vaccine, Vaccine, 17(9):2446–52 (1999).

Murano EA, et al., Role of Respiratory–burst products from polymorphonuclear leukocytes in the antitumor activity of Propionibacterium acnes vaccine, Cancer Immunol, Immunother., 19(1):7–16 (1989).

Neifeld JP et al., Adjuvent corynebacterium parvum immunotherapy for squamous cell epitheliomas of the oral cavity, pharynx, and larynx, J. Surg. Oncol., 28(2):137–45 (1985).

Roszkowski W et al., Effect of three strains of propionibacteria (P. granulosum , P. avidum, P. acnes) and cell–wall preparations on lymphocytes and macrophages, Zentralbl. Bakterio. A., 246(3):393–404 (1980).

Van Kampen KR, Immunotherapy and Cytokines, Seminars in Vet. Med. and Surgery (small animal), 12(3):186–92 (1997).

Wu Y et al., Increased endogenous N–nitrosamine and nitrate formation by induction of nitric oxide synthase in rats with acute hepatic injury caused by Propionibacterium acnes and lipopolysaccharide administration, Carcinogenesis, 14(1):7–10.

Zgorniak–Nowosielska I. et al., Protection of mice against vaccine and herpes simplex virus infection by Propionibacterium acnes, Arch. Immunol. Ther. Exp. (Warsz), 37(3–4):431–2 (1989).

* cited by examiner

TREATMENT OF DERMAL TUMORS, WARTS, AND VIRAL INFECTIONS OF THE RESPIRATORY TRACT IN HUMANS USING HEAT-KILLED *P. ACNES*

This application claims benefit of provisional appln. 60/159,567 filed Oct. 15, 1999.

FIELD OF THE INVENTION

The present invention relates to methods to treat viral infections, dermal tumors, and warts in humans using heat-killed bacterial compositions. Specifically, it relates to the subcutaneous or intralesional administration of heat-killed *Propionibacterium acnes* (*P. acnes*), to treat dermal tumors and warts, and to the oral administration of heat-killed *P. acnes* to treat virus induced infections of the respiratory tract in humans.

BACKGROUND OF THE INVENTION

The maintenance of a healthy and competent immune system is a prerequisite for resistance to and elimination of infectious and neoplastic diseases. Bacteria and their derivatives were among the first substances to be recognized as immunostimulators and are used as adjuvants in vaccines to boost the humoral immune response (e.g., complete Freund's adjuvant). Bacteria have also been used as non-specific enhancers of the immune system to increase resistance and rejection of cancers, parasites, and infectious organisms.

Gram positive, whole-cell bacteria such as *Propionibacterium acnes, Propionibacterium avidum, Propionibacterium lymphophilum, Propionibacterium granulosum, Cornynebacterium parvum* and *Arachnia propionica,* when inactivated have been shown to be potent non-specific immune stimulants in animals and humans. Specifically *Propionibacterium acnes* (*P. acnes*) has been shown to stimulate antineoplastic activity, adjuvant activity, antiviral activity, antibacterial activity, and stimulate hematopoiesis.

Preparations of *P. Acnes* have been shown to act as non-specific stimulators of immunogenic responsiveness in vivo. *P. Acnes* is known to act by stimulating macrophages and neutrophils, initiating endogenous production of lymphokines (including IL-2 and various interferons), and enhancing killer cell activity. The intranasal inoculation of mice with *P. acnes* have been shown to activate pulmonary macrophages (Jackson R A, et al., *J Leukoc. Biol.,* 40(5): 575–87, 1986). At the cellular level, *P. acnes* acts upon monocytes and lymphocytes and improves the functional interaction between these cells (M. T. Scott, *Cell Immunol.,* 17:141, 1975).

*P. acnes* also functions as an immune adjuvant to weakly antigenic substances. These properties, while not completely understood, play an important role in regulation of the immune response. One mode of the interaction of inactivated *P. acnes* with the immune system is through its stimulation of the reticuloendothelial system (RES), i.e. liver, spleen, lymph nodes, lungs, and bone marrow (C. Adlam, and M. T. Scott, *J. Med Microbiol,* 6:621 (1973), N. H. McBridge et al., *Cell Immunol.,* 7:290 (1973)).

This activity elicits enhanced resistance to bacterial and viral infections, and also to certain tumors. This mode of action appears to be the activation of macrophages followed by the recruitment of lymphocytes. The particulate nature of *P. acnes* appears important for macrophage activation. Unlike some synthetic biological response modifiers (BRM's), bacteria in vivo are fully degraded and catabolized in the body without the formation and excretion of toxic metabolites or retention of residues. This has obvious therapeutic advantages for *P. acnes,* and contributes to the therapeutic and prophylactic use of *P. acnes* against infectious diseases.

In animals, stimulation of the immune system results in short term protection against infection with certain viruses and bacteria. Used therapeutically in animals with chronic skin and respiratory disease, *P. acnes* shortens the course of the disease.

The anti-tumor activity of *P. acnes* has been studied in mice and other animals. Tumor cells injected into Balb/c mice together with heat-killed *P. acnes* cells were rendered nontumorigenic (Murano E A, et al, *Cancer Immunol Immunother,* 29(1):7–16, 1989). The preventive effect of *P. acnes* on metastasis in mice rendered tolerant to tumor-associated transplantation antigens (TATA) has been detailed (Fujiwara H, et al., *Gann,* 71(5):692–8, 1980). Heat-killed suspension of several *P. acnes* strains were prepared and studied for their protective activity against viral infections in mice and for their immunomodulating properties (Zgorniak-Nowosielska I, et al, *Arch Immunol Ther Exp* (*Warsz*), 37(3–4):431–42, 1989).

There has been considerable data collected on the use of *P. Acnes* in domestic animals. In a randomized study conducted for the treatment of equine respiratory disease (ERDC), complete recovery within a 14 day period was observed in horses treated intravenously with *P. acnes* (D. R. Evans et al., *Equine Practice,* 10:17, 1988; C. D. Vail et al., *Vet. Review,* November/December: 399, 1990). Additionally, inactivated *P. acnes* has also been shown to be a biological response modifier for treatment of non-specific respiratory diseases in horses where upon administration of *P. acnes* it was shown that CD4+ lymphocyte expression and lymphokine activated killer cell (LAK) activity increased (Flaminio M J, et al, *Vet Immunol Immunopathol,* 63(4):303–15, 1998).

In a randomized, double blinded, placebo controlled study, dogs with a significant skin disease (chronic recurrent pyoderma) were treated with antibiotics plus *P. acnes* with significant improvement or complete remission of the lesions (A. Becker et al., J. Vet Intern. Med. 13:26 (1989)).

*P. acnes* has been extensively used as a veterinary therapeutic in cattle with papilloma (warts) where the warts had been intralesionally injected with *P. acnes* (H. Hall et al., *Therapeutic Immunology,* 1:319, 1994). While, lesions in the control group which were injected with saline showed no regressions at the end of 16 weeks, 100% of the injected lesions in the treatment group had completely regressed at the end of 16 weeks.

Use of *P. acnes* in humans has, in general been limited to treatment of neoplastic diseases and pleural effusions with some limited success. Additionally, *P. acnes* has been administered orally in the rations of food production animals to promote better health through cell-mediated immunity and weight gain (U.S. patent application Ser. No. 08/912,026). It has been used experimentally in people to treat various cancers, plural effusion and chronic obstructive pulmonary disease. It has been used experimentally as an adjuvant with vaccines.

Based on these findings, a veterinary preparation of *P. acnes* was used as an injectable therapeutic agent against plantar warts caused by the human papilloma virus. However, significant pain upon injection was observed caused due to the alcohol content of the preparation. Thus, a preparation of *P. acnes* is needed that causes the regression of warts and dermal tumors in humans, but which may be administered without undue pain or harm to the patient. Additionally, this preparation must be administered via a route that allows regression of the warts while minimizing pain to the patient.

Although *P. acnes* has been used to treat respiratory diseases in horses and cattle, the oral administration of *P. acnes* with efficacy in humans has not been previously demonstrated. There is a need for a *P. acnes* preparation that can be safely administered to humans for the treatment of viral infections of the respiratory tract.

*P. acnes* preparations have been administered primarily through intravenous, intraperitoneal, or intrathoracic routes. However, they may also be administered orally, subcutaneously, or intralesionally depending on the type of infection and the determined dosage. *P. acnes* has been used at higher dose levels in experimental animals to study the release of nitric oxide by cells or the liver and other body tissues, and has been combined with vaccines as an adjuvant for subcutaneous or intramuscular injection. Ethanol-saline suspended preparations of heat-killed *P. acnes* for veterinary use in treating pyoderma, a bacterial infection in dogs, and respiratory infections in horses have been used. However, these preparations had to be administered intravenously in order to be efficacious. In another case, a feed additive consisting of dried *P. acnes* mixed with feed rations was given to baby pigs which subsequently exhibited decreased mortality, increased weight gain and feed conversion. However, optimization of the route of administration for the treatment of dermal warts, tumors, and viral infections of the respiratory tract in humans has not hitherto been conducted.

In order to efficaciously administer the *P. acnes* preparation, an optimal mode of inactivation of the *P. acnes* preparation is also needed. Although, suspending the *P. acnes* in an ethanol-saline suspension causes inactivation of *P. acnes,* the presence of ethanol causes discomfort in humans. Thus, there is a need to safely and adequately inactivate the *P. acnes* without any undue loss in activity. Heat-killing is an efficacious method of inactivating *P. acnes.* However, there is a need to develop a method of heat-killing that adequately inactivate the *P. acnes* while maintaining desired levels of activity.

SUMMARY OF THE INVENTION

This is an invention to induce regression of a virally induced dermal tumor, especially plantar warts for which painful surgical removal or chemical burning are the most common methods of removal. These alternate methods cause severe pain and limit mobility to a majority of patients receiving these treatments. It is also an invention to treat and hasten recovery from virally induced infection of the respiratory tract using autoclaved *P. acnes* through a novel route of administration, previously not demonstrated in man, that of oral administration.

This invention also relates to the preparation of an alcohol-free, terminally sterilized saline-suspended *P. acnes* product that causes the regression of dermal tumors, and plantar warts in humans. Terminal sterilization may be conducted through the process of autoclaving. In another embodiment of the product, an anesthetic such as lidocaine is added to the *P. acnes* product. The invention also relates to a novel intralesional administration of the *P. acnes* product into plantar warts, or other warts caused by the human papilloma virus causing regression of such warts, and the subcutaneous administration of the *P. acnes* product resulting in a systemic regression of warts.

DETAILED DESCRIPTION OF THE INVENTION

This invention relates to the preparation, administration, and use of an inactivated bacterial product to induce regression of virally induced dermal tumors and warts, and to effectively treat virally induced infections of the respiratory tract. The warts may be plantar, genital, or surface warts anywhere on the skin or mucosal surface of the body, or those caused by the human papilloma virus.

The bacteria used for practicing the invention may be selected from the group consisting of *Propionibacterium acnes, Propionibacterium avidum, Propionibacterium lymphophilum, Propionibacterium granulosum, Cornynebacterium parvum* or *Arachnia propionica.* Preferably, the bacteria used for practicing the invention are selected from the Propionibacterium family. Most preferably, the bacteria used for practicing the invention is *Propionibacterium acnes* (*P. acnes*). Thus, *P. acnes* will be the bacterium referred to throughout the description, although any of the bacterial species claimed can be substituted. However, the statements contained in this description should apply to each of the bacteria claimed unless otherwise indicated, since all of the claimed bacteria are expected to have the same results due to their taxonomic similarity. Although it is now recognized that *Cornynebacterium parvum* (*C. parvum*) is thought to be synonymous with *P. acnes,* it has been included in the list due to the use of the name that still exists in the art.

In the present invention, a method for preparing a saline suspension of heat-killed *P. acnes* with demonstration of potency through a laboratory animal challenge model is disclosed. It has been determined that heat-killing, which usually destroys or alters the antigens needed to stimulate the immune responses, does not destroy the potency of the autoclaved *P. acnes* product. Furthermore, as shown in laboratory animal potency tests, the addition of an anesthetic such as lidocaine to the autoclaved *P. acnes* product does not destroy the potency of the *P. acnes* product.

*P. acnes* is known to be commercially available in forms such as an injectable solution (e.g., ImmunoRegulin® or EqStim® by Neogen Corp. (Lansing, Mich.)), but it may also be isolated and cultured by known, standard bacterial procedures or obtained from national culture collections. The bacteria used were obtained from ImmunoVet Corp. (Tampa, Fla.) who produced them under U.S.D.A. Product Code 9350.00. The bacteria may also be obtained from Neogen Corp. (Lansing, Mich.). The bacteria may be provided wet or dry. A dry form may be prepared by standard drying methods known to a person skilled in the art, such as freeze-drying or evaporation.

*P. acnes* may be manufactured by laboratory processes known in the art. *P. acnes* may be isolated and cultured by standard cell culture methods. The *P. acnes* product is prepared by culturing *P. acnes* on solid or in liquid media at a temperature of 36° C.+/−2° C. for 24 to 192 hours, depending on the culture conditions. *P. acnes* may be grown on plates, e.g., agar plates containing various nutrients, or in bioreactors. The bioreactors include stationary culture flasks, shaker flasks, standard fermentors, hollow fiber reactors, perfusion reactors, plug flow reactors, etc., containing a fermentation broth with nutrients in dissolved form such as glucose, starches, tryptic soy broth, hormones, coenzymes, and optionally serum. *P. acnes* is then collected using standard separation methods such as centrifugation, and tested for purity by immunofluoresecence or biochemical testing.

The *P. acnes* is dried while subjected to heat sufficient to inactivate and kill it. Heat-killing is preferably conducted by heating the *P. acnes* in a water bath at 74° C. to 90° C. for 60 to 90 minutes. The *P. acnes* is then weighed and suspended in a sterile saline solution at a concentration of 0.005 to 10 mg/ml. The exact concentration is determined by the proposed use of the product, be it the treatment of warts or viral infections of the respiratory tract. The saline solution comprises sodium chloride in a buffer selected from the group consisting of alkaline metal phosphate or citrate buffers, such as sodium phosphate, potassium phosphate, sodium citrate, and potassium citrate, or sodium chloride in dI water. Preferably, the concentration of the sodium chloride is 0.85% w/v, more preferably the concentration of the sodium chloride is 0.9% w/v.

Optionally, the *P. acnes* may be mixed with carriers and fillers, and brought into the form of a therapeutically enteric pharmaceutical composition. Suitable carriers are sugars including but not limited to lactose, saccharose, mannitol, or sorbitol; cellulose preparations, amino acids such as glycine, binders such as starch pastes that use corn, wheat, rice or potato starch, gelatine, methylcellulose, hydroxypropylmethylcellulose, and sodium carboxymethylcellulose.

Optionally, an anesthetic may be added to the *P. acnes* product to induce local anesthesia when administered to the patient. Local anesthetics are drugs that block the generation and propagation of impulses in excitable tissues, most notably the spinal cord, spinal nerve roots, and peripheral nerves, but also skeletal muscle, cardiac muscle, and the brain. Preferably, the anesthetic is chosen from the group consisting of aminoamides, such as lidocaine (xylocaine), and aminoesters such as 2-Chloroprocaine. Preferably, the local anesthetic is lidocaine (xylocaine). Preferably, the anesthetic is added to the *P. acnes* preparation to make a final concentration of 0.25% to 5.0% v/v, more preferably at a final concentration of 0.5% to 2.5% v/v, and most preferably at a final concentration of 1% to 2% v/v.

The *P. acnes* may be lyophilized at any step in the preparation process depending on whether the final pharmaceutical formulation is to be stored as a liquid with stabilizing fillers, or as a lyophilized solid.

Once the *P. acnes* product is in the final vial, it is terminally sterilized by heating to 121° C., for 20 minutes, at a pressure of 15 psi.

The *P. acnes* product may be tested for potency using standard animal inoculation tests which consists of pre-inoculating the animal with the product, followed by a lethal challenge of a known bacterial pathogen at 1–7 days which kills at least 75% of the non-inoculated control animals. The dosage units tested are equivalent to $10^9$–$10^{13}$ *P. acnes,* preferably $10^{10}$–$10^{12}$ *P. acnes.* Lidocaine (xylocaine) is added at a dosage that does not affect the potency of the formulation. The laboratory animal potency tests demonstrated that this local anesthetic does not adversely affect the potency of the product.

In the present invention, the autoclaved *P. acnes* product is administered intralesionally or subcutaneously to cause the regression of plantar warts in humans. The *P. acnes* product retains activity once autoclaved and once injected, and may be used with or without the addition of an anesthetic. However, the novel addition of anesthetics like lidocaine to this immune modulating preparation of *P. acnes* retains the potency of the *P. acnes* while preventing pain upon injection. The warts may be plantar, genital, or surface warts located anywhere on the skin or mucosal surface of the body. The subcutaneous route of administration of the *P. acnes* product causes a systemic reaction that causes long-term warts to completely regress. Specifically, the subcutaneous injection of the product into the arm induces the regression of warts located on the hands or feet of the patients receiving the injection. Thus, it has been determined that at doses prescribed for intralesional injections, subcutaneous injection may also be effective in causing a systemic regression of the warts. Multiple injections may be made intralesionally or subcutaneously for the purpose of treating plantar warts. Repeated doses in animals or humans have not resulted in any cumulative toxicity. Since the plantar warts are the most difficult variety of the human papilloma to treat, multiple injections may be required over time. However, a single injection may cause regression of the wart. For the regression of warts, the *P. acnes* is administered at a dose of 0.001 to 5 mg per dosage, preferably at a dose of 0.005 to 2.5 mg per dosage, and more preferably at a dose of 0.01 to 1 mg per dosage.

The *P. acnes* product may also be used to treat chronic complications of the respiratory tract due to viral or bacterial infections where symptomatic coughs are persistent. The *P. acnes* product is orally administered as a treatment for acute or subacute viral infections of the respiratory tract in people, at a dose range of 0.1 to 10 mg, and more preferably at a dose range of 0.5 to 5 mg. Oral administration of the heat killed, terminally sterilized *P. acnes* saline product will hasten recovery from virally induced infections of the upper and lower respiratory tract. Optionally, an FDA approved natural or synthetic flavoring is added to the final product to make the administered product more palatable. The FDA approved natural flavorings are listed in the Code of Federal Regulations, 21 CFR 172.510. The synthetic flavorings are listed in 21 CFR 172.515.

The complete disclosure of all patents, patent documents, and publications cited herein are incorporated by reference. The detailed descriptions and examples herein have been given for clarity of understanding only. No unnecessary limitations are to be understood therefrom. The invention is not limited to the exact details shown and described, for variations obvious to one skilled in the art will be included within the invention defined by the claims.

EXAMPLE 1

Treatment of Sore Throat, Ear Ache and Cough by Oral Administration of Autoclaved, Heat-killed *P. acnes*

A sterile saline suspension of non-viable *P. acnes,* terminally autoclaved for 15 minutes at 15 psi, was orally administered to patients to impede the advancing clinical signs of upper and lower respiratory tract infections, clinically manifested as sore throat, ear ache, and cough.

*P. acnes* was orally administered to two patients to treat the onset of symptoms of a sore throat and ear inflammation. In each case, the treatment consisted of 2 ml of a saline suspension of non-viable, heat-killed and terminally sterilized *P. acnes* at a concentration of 0.4 mg per ml. The success of the treatment demonstrates the efficacy of orally administer *P. acnes* to minimize infections of the respiratory tract in humans. Either one dose or more may be used safely to treat the symptoms of disease.

The first patient was a 60-year old Caucasian male weighing 190 pounds. The patient was treated with the suspension on two separate occasions. The patient had symptoms of a sore throat and ear inflammation. The treatment was administered orally. The material was held at the back of the mouth for about 1 minute before swallowing. In about 8 to 12 hours following the treatment, the patient felt somewhat flushed, a symptom that could be related to the infection or to immunostimulation. Within 24 hours, the onset of the sore throat and the ear infection diminished. Within 2 days, the patient was healthy with no remaining symptoms of the sore throat and ear infection.

In October, 1998, the patient displayed symptoms of sneezing, coughing, nasal discharge, sore throat, and aching ears. The treatment was administered orally. The material was held at the back of the mouth for about 1 minute before swallowing. Within the following 24 hour period, the patient again noted a slight febrile response. A second dose, similar to the first dose, was administered twenty-four hours following the first dose. No febrile response was observed after this administration. No symptoms of inflammation of the throat and ears were observed after the first day. However, mild coughing and nasal discharge continued on the second day. On the third day, the symptoms began to abate and on the fourth day, they were entirely gone.

The second patient was a 32-year old Caucasian female weighing about 140 pounds. The patient had a hoarse voice and complained of an ear ache and sore throat. She was given a similar suspension in the same amount as mentioned above. She did not express any adverse reactions or any symptoms other than those relating to her upper respiratory tract infection. The day following treatment, her throat felt better and within two days thereafter, she was again healthy.

This finding demonstrates the efficacy of orally administer *P. acnes* to minimize infections of the respiratory tract in people. Either one dose or more may be used safely to treat the symptoms of disease.

EXAMPLE 2

Preparation of *P. acnes*

*P. acnes,* grown on solid or in liquid media at a temperature of 36° C. for 7 days is separated, tested for purity (by immunofluorescence) and/or biochemical testing, dried while subjected to heat sufficient to kill it, weighed, and suspended in sterile saline at the desired concentration. In the final vial, the product is terminally sterilized for 20 minutes at 15 psi. Or the product can be modified by (through sterile filling) the addition of lidocaine at the desired concentration to induce local anesthesia when injected. The product is then tested for potency using the laboratory animal inoculation test which consists of pre-incubation with the product and followed several days later by a lethal challenge of a known bacterial pathogen which kills at least 75% of the non-inoculated control animals.

EXAMPLE 3

Evaluation of the Safety of Injecting Heat-killed *P. acnes* into Volunteers with Plantar Warts The purpose of this Phase I Safety Study was to evaluate the safety of injecting heat-killed, *P. acnes* into volunteers with plantar warts. Two routes of administration were utilized, intralesional and subcutaneous. Two dose levels of experimental product (0.1 mg and 0.2 mg.) were injected. The control group was injected intralesionally with sterile saline at a volume consistent with the 0.2 mg amount of *P. acnes.* Safety parameters were assessed by changes or lack of changes in physical, hematologic, biochemical, and immunologic parameters. The lot # of the Test Article was 022497 and the Placebo was lot #KVK794220. Concentration of *P. acnes* was 0.4 mg. per milliliter. In order to test for reactions resulting in repeated injections, the volunteers received a series of three injections at intervals of one week. The patients were randomized upon entry to the study and the study was placebo controlled and blinded to the patient, but not to the investigator. The patients were monitored for four weeks following the initial injection.

Anticipated reactions were monitored along with changes in the blood cells, blood chemistry and in the urine. Provisions were in place to focus on any unexpected adverse reactions. The various systemic events monitored included elevated temperature, headache, muscle pain, weakness, chills, nausea, and at the injection site, pain, swelling, redness and discoloration. These are reported on each patient, grouped by treatment and recorded by severity. A summary by treatment groups of the anticipated reactions by number of patients and severity is provided. Separate summary sheets of the observed hematological, chemical and urine changes are also provided for each patient.

In the overall evaluation of the clinical signs designated as anticipated events, in those volunteers who designated the severity as "severe", the total events were ranked in the following order for the combined groups: elevated temperature above 100° F., (21), pain at the injection site (15), headaches (5), chills (4), muscular pain (4), discoloration (3), weakness (2), nausea (2), swelling (2), and redness (2).

Where the anticipated events were designated as "moderate", the events were ranked as follows for the combined groups: temperature between 98.0 and 99.9° F., (104), pain at the injection site (30), swelling (27), weakness (9), chills (8), headache (7), treatment groups collectively, there were 8/30 complete regressions, 6/30 that were reduced in size, 10/30 that were not changed in size, 2/30 that were enlarged and 4/30 that were lost to follow-up. In the control group, there were no regressions, no reductions in size, ⅔ that were not changed in size and ⅓ that was enlarged.

These studies show that while concentrations below 0.4 mg/ml are adequate, the volumes required for efficacy are subsequently higher. Therefore, the test material should be concentrated above 0.4 mg per milliliter in order to reduce the volume of intralesional injections. Since there were a number of complete regressions in the groups were the material was administered subcutaneously, both intralesional and subcutaneous administration separately, or in combination, are efficacious.

EXAMPLE 4

Clinical Toxicities of *P. acnes* in Human Subjects

*P. acnes,* manufactured within the State of Florida (ImmunoMed Corporation) has been administered intravenously to 21 cancer patients in a completed Phase I study conducted under Florida law. The patients were comprised of 14 males and 7 females, age 38 to 73 years (median=56). The dosage per injection ranged from 25 $\mu$g to 800 $\mu$g, and the total dosage ranged from a low of 50 $\mu$g to a high of 8525 $\mu$g.

A total of 256 injections were administered to these patients, and 44 were associated with toxicity (17.2%). Toxicities reported included chills (24/256—9.4%), fever (22/256—8.6%), nausea (10/256=3.9%), myalgia (4/256—1.6%), malaise (2/256—0.8%), and lightheadedness (2/256— 0.8%). There was no injection site toxicity reported.

In another experiment with *P. acnes,* 3 healthy male volunteers were administered the immunostimulant I.V. Two received 0.1 mg (0.0012 mg/kg) and the third received 0.2 mg (0.0023 mg/kg). Fever, chills, malaise, lethargy, and slight muscle soreness were experienced by all three individuals beginning 12–18 hours following injection. One individual, who received 0.2 mg, experience slight nausea without vomiting. Symptoms abated within 24 hours after onset. One individual received 0.1 mg was administered a second injection of 0.1 mg 27 days after the first injection. Only a slight fever (1° F. increase) was recorded with no other symptomatology.

Intralesional and subcutaneous injections of the test material have minimally associated toxicities. Intravenous administration should have toxicities similar to those reported previously.

What is claimed is:

1. A method of inducing the regression of dermal tumors and warts caused by the human papilloma virus in humans, said method comprising the step of administering a bacterial product comprising heat-killed, terminally sterilized *Propionibacterium acnes.*

2. The method of claim 1, wherein the bacterial product comprises heat-killed *Propionibacterium acnes.*

3. The method of claim 1, wherein the bacterial product further comprises an anesthetic.

4. The method of claim 3, wherein the anesthetic is selected from the group consisting of aminoamides and aminoesters.

5. The method of claim 3, wherein the anesthetic is lidocaine.

6. The method of claim 1, wherein the bacterial product further comprises carriers and fillers.

7. The method of claim 6, wherein the carriers comprise sugars selected from the group consisting of lactose, saccharose, mannitol, sorbitol, and cellulose preparations.

8. The method of claim 6, wherein the carriers comprise amino acids.

9. The method of claim 6, wherein the fillers are selected from the group consisting of starch pastes that use corn, wheat, rice or potato starch, gelatin, methylcellulose, hydroxypropylmethylcellulose, and sodium carboxymethylcellulose.

10. The method of claim 1, wherein the bacteria are heat-killed by the process of heating the bacteria in a water bath at 74° C. to 90° C. for 60 to 90 minutes.

11. The method of claim 1, wherein the bacterial product is suspended in a saline solution.

12. The method of claim 11, wherein the saline solution comprises sodium chloride in deionized water.

13. The method of claim 11, wherein the saline solution comprises sodium chloride in a buffer.

14. The method of claim 13, wherein the buffer is selected from the group consisting of alkaline phosphates and alkaline citrates.

15. The method of claim 1, wherein the bacterial product is administered intralesionally.

16. The method of claim 1, wherein the bacterial product is administered subcutaneously.

17. The method of claim 1, wherein the bacterial product is administered at 0.001 to 5 mg per dosage.

18. The method of claim 1, wherein the bacterial product is administered at 0.005 to 2.5 mg per dosage.

19. The method of claim 1, wherein the bacterial product is administered at 0.01 to 1 mg per dosage.

* * * * *